United States Patent [19]
Ekman

[11] 3,994,174
[45] Nov. 30, 1976

[54] DEVICE FOR MEASURING THE DENSITY OF LIQUIDS

[75] Inventor: Lennart Ekman, Danderyd, Sweden

[73] Assignee: AB Källe-Regulatorer, Saffle, Sweden

[22] Filed: Mar. 20, 1975

[21] Appl. No.: 560,668

[30] Foreign Application Priority Data
Mar. 25, 1974 Sweden............................ 7403978

[52] U.S. Cl. .................................. 73/452; 73/453; 318/676
[51] Int. Cl.² ............................................ G01N 9/22
[58] Field of Search .......... 73/451, 452, 453, 517 B; 318/638, 656, 657, 658, 676

[56] References Cited
UNITED STATES PATENTS

| | | | |
|---|---|---|---|
| 2,695,165 | 11/1954 | Hansen | 73/517 B |
| 3,040,585 | 6/1962 | Chatel et al. | 73/453 |
| 3,126,745 | 3/1964 | Lutke | 73/453 |
| 3,377,869 | 4/1968 | Glassey | 73/453 |

*Primary Examiner*—James J. Gill
*Attorney, Agent, or Firm*—Sughrue, Rothwell, Mion, Zinn & Macpeak

[57] ABSTRACT

A device for measuring the density of liquids. A float provided with a piece of soft iron on one side and with a permanent magnet on the other side is movably disposed in a housing through which a liquid may flow. The soft iron is surrounded by a differential winding, and the permanent magnet is surrounded by two windings with opposing fluxes and having substantially the same numbers of ampere-turns. An output lead from the differential winding is connected to the windings surrounding the permanent magnet over an amplifier. A measuring instrument connected between the amplifier and the windings surrounding the permanent magnet provides an indication of the density of the liquid flowing through said housing.

2 Claims, 2 Drawing Figures

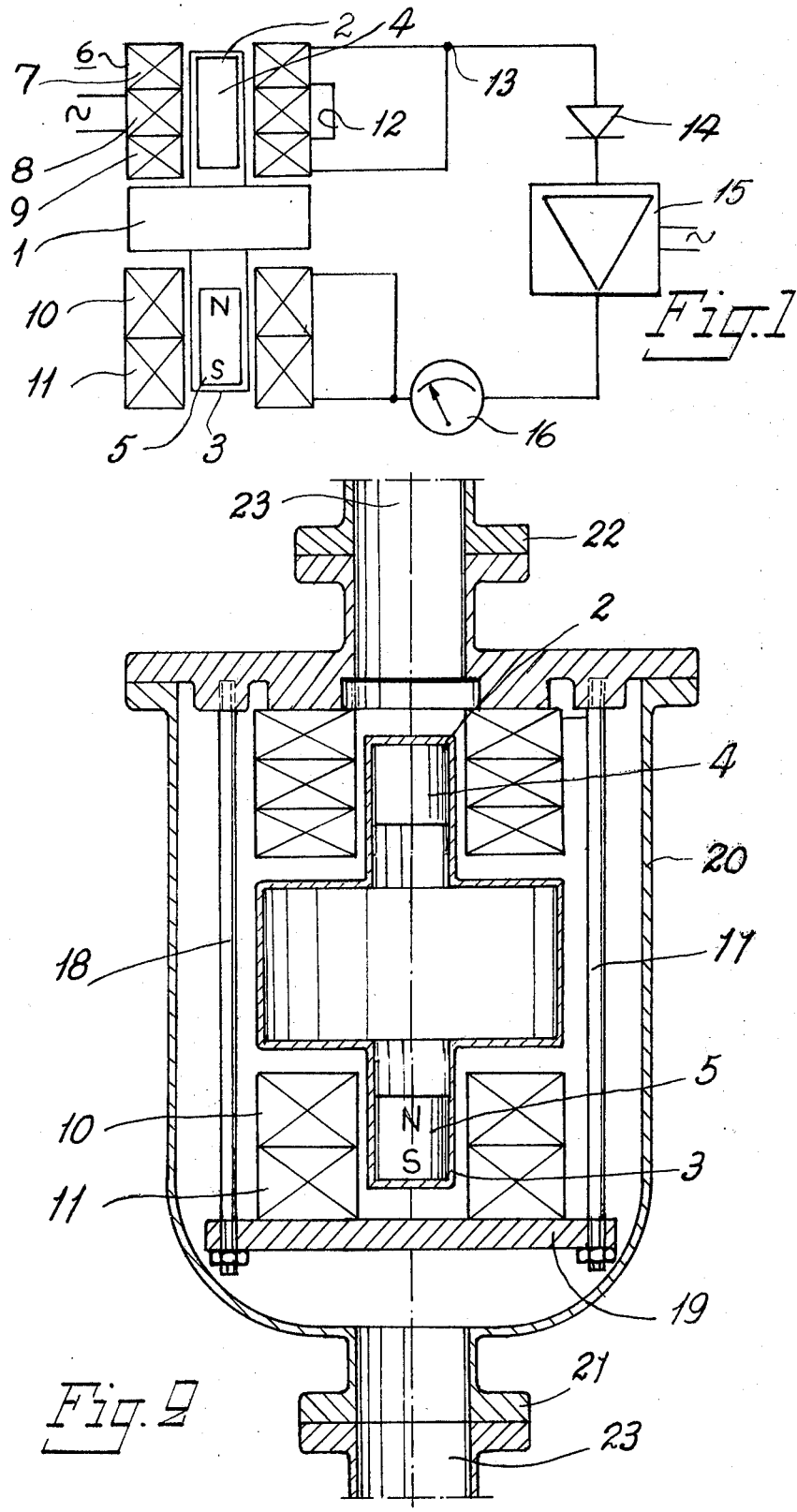

DEVICE FOR MEASURING THE DENSITY OF LIQUIDS

BACKGROUND OF THE INVENTION

1. Field of the Invention

This invention refers to a device for measuring the density of liquids and more specifically to a device for measuring the density of black liquor.

2. Description of the Prior Art

Densimeters of magnetic type are known. As an example of such meters the inventive subject of Swedish Pat. Spec. No. 220,181 may be mentioned, said patent specification illustrating a magnetic densimeter for liquids, wherein a float immersed in the liquid is at its lower end provided with a cylindrical magnet which creates a current in a differential transformer when the float changes its position as the result of a change of density in the liquid. The current from the differential transformer is supplied over an amplifier, a rectifier and a filter to a coil, which in turn attracts the cylindrical magnet so that a new position of equilibrium is achieved in due course.

However, a device of the described type is restricted with regard to its range of measuring, as the device primarily is a laboratory instrument by means of which it is possible to measure the density of liquids of comparatively low viscosity. The measuring must be carried out in a shunted flux, which never provides correct results, as the flux conditions then will have been changed by the shunting.

In certain industrial applications the known devices and methods are not satisfactory, namely for measuring the density of liquids having higher degrees of viscosity, for example black liquor, with the purpose of such measuring being to provide an indication of the content of dry matter in the liquid.

Indeed, densimeters for industrial settings already exist, said densimeters also being capable of being utilized for black liquor in certain cases, but these densimeters have various disadvantages. As examples of this type of densimeter mention may be made of radioactive densimeters, U-tube scales and bubble tubes. The radioactive densimeter may be utilized only for high-viscosity liquor, and furthermore it is in a high price range. Contrary to the radioactive meter, the U-tube scale is solely appropriate for low-viscosity liquor because of the existing danger of contamination and clogging. The bubble tube has substantially the same disadvantages as the U-tube scale.

SUMMARY OF THE INVENTION

The present invention has the object of providing a magnetic densimeter which to advantage may be utilized industrially for measuring the density of liquids having high viscosities. Advantages as compared to the densimeter described by way of introduction are achieved in accordance with the invention not only as the result of it being possible to measure the density in the main portion of the liquid in accordance with the invention and hence achieving an entirely correct measuring value, as the flux conditions have not been changed, but also as the result of greater setting forces being provided by means of the invention. Furthermore, the densimeter of the invention is low-priced and can withstand environmental strains. It is not restricted to use for measurements with respect to high-viscosity liquor but may also be utilized for low-viscosity liquor.

The invention more specifically refers to a device for measuring the density of liquids, particularly for measuring the density of a flowing liquid, with a float being movably disposed in a conduit for the flowing liquid whose density is to be measured. In said device the float is provided with a piece of soft iron and a permanent magnet. The piece of soft iron is surrounded by a differential winding, and the permanent magnet is surrounded by two windings with opposing fluxes and having substantially the same numbers of ampere-turns. Also, the output leads from the differential winding are connected over an amplifier to the windings surrounding the permanent magnet. Furthermore, a measuring instrument may be connected between the amplifier and the windings surrounding the permanent magnet.

BRIEF DESCRIPTION OF THE DRAWING

The invention will be described more specifically in the following with reference to the accompanying drawing, in which FIG. 1 diagrammatically shows a circuit diagram including the densimeter of the invention and FIG. 2 illustrates an embodiment of the densimeter in accordance with the invention on a larger scale.

The same reference numerals have been used in both of the figures wherever possible.

DESCRIPTION OF THE PREFERRED EMBODIMENT

FIG. 1 shows a float 1 of such design that together with portions connected thereto, which will be described below, it assumes a position of equilibrium in a flowing liquid having a density of a predetermined magnitude, for example between 0.5 and 5.0, and preferably approximately 1.2 – 1.4. The float 1 may have the form of a short cylindrical drum which is provided with an upwardly directed extension 2 and an extension 3 directed downwardly along its axis of symmetry, said extensions 2 and 3, respectively, having substantially smaller diameters than the float 1. A piece of soft iron 4 is disposed in the upwardly directed extension 2, and a permanent magnet 5 is disposed in the downwardly directed extension 3 with its poles disposed in accordance with FIG. 1. The float may to advantage be made of stainless steel which is substantially inert to magnetic actuation.

The design of the densimeter may be seen more specifically in FIG. 1, which shows that the float extension 2 with the enclosed piece of soft iron 4 is surrounded by a differential winding 6 comprising three individual windings 7, 8 and 9. The downwardly directed extension 3 of the float, which contains the permanent magnet 5, is surrounded by two windings 10 and 11. As is indicated in FIG. 1, the intermediate winding 8 of the differential winding 6 is connected to alternating current means. The inner ends of its two outer windings 7 and 9, respectively, are interconnected by means of a lead 12, and the outer ends of said windings are interconnected at the junction 13 which is connected to a rectifier 14, which in turn is connected to an amplifier 15 being connected to each of the coils 10 and 11. A pointer instrument 16 comprising an ampere meter is connected in the lead between the amplifier 15 and the junction of the coils 10 and 11.

As may be seen in FIG. 2 the coils 10 and 11 cooperating with the permanent magnet are mechanically supported by a base plate 19 which is suspended by rods 17 and 18, with the entire float device and the associated windings forming a unit which is built into a housing 20 which is adapted to be connected in a conduit 23 with a main flux flowing from the bottom of FIG. 2 to the top by means of flanges 21 and 22.

The measuring device operates in the following manner.

Liquid flowing to conduit 23 and having a definite density, for example approximately 1.25, keeps the float in equilibrium. If the density of the liquid is changed, this will cause the position of float 1 to change, whereby the piece of soft iron 4 will induce a voltage in the differential winding 6 so as to provide a current which is rectified in rectifier 14 and which is passed over amplifier 15 to coils 10 and 11 through instrument 16. The coils 10 and 11 should have substantially the same numbers of ampere-turns, with the resulting flux in these coils causing float 1 to be reset so that equilibrium occurs. The deflection of instrument 16, which is proportional to the current, is linear, and the instrument 16 may to advantage be graduated on a density scale.

Because of the opposing windings 10 and 11 permanent magnet 5 never becomes demagnetized. Furthermore, setting forces of considerable magnitude are achieved. As has been indicated above an appropriate range for density measurements with the relevant instrument lies between 0.5 and 5.0.

The invention is not restricted to the embodiment described above and illustrated in the drawing, and this embodiment merely comprises an example of the invention and its application.

I claim:

1. In a device for measuring the density of liquids having a housing with a fluid inlet and a fluid outlet, said fluid inlet and fluid outlet being operably coupled to a conduit carrying the liquid whose density is to be measured, a movable float disposed in said housing having an armature at one end and a permanent magnet at the other end thereof, a differential transformer positioned in said housing surrounding said armature, a source of electrical power coupled to one side of said differential transformer, the improvement comprising: rectifier means coupled to the other side of said differential transformer, an amplifier coupled to said rectifier, a pair of windings with opposing fluxes, each having substantially the same number of ampere turns surrounding said permanent magnet and coupled to said amplifier wherein rectified current produced as a result of movement of said armature relative to said differential transformer is supplied to said pair of windings to restore said permanent magnet to a position of equilibrium relative to said pair of windings without demagnetizing said permanent magnet.

2. A device in accordance with claim 1, wherein a measuring instrument is connected between the amplifier and the windings surrounding the permanent magnet.

* * * * *